(12) United States Patent
Rickard et al.

(10) Patent No.: US 6,439,439 B1
(45) Date of Patent: Aug. 27, 2002

(54) BONE CEMENT DELIVERY APPARATUS AND HAND-HELD FLUENT MATERIAL DISPENSING APPARATUS

(75) Inventors: Thomas A. Rickard, Missoula; Randy Scot Wills, Florence; Ronnie Burchett, Missoula, all of MT (US)

(73) Assignee: Telios Orthopedic Systems, Inc., Missoula, MT (US)

( * ) Notice: Subject to any disclaimer, the term of this patent is extended or adjusted under 35 U.S.C. 154(b) by 0 days.

(21) Appl. No.: 09/760,179

(22) Filed: Jan. 12, 2001

(51) Int. Cl.[7] ............................................... B67D 5/00
(52) U.S. Cl. .................... 222/391; 222/327; 606/93
(58) Field of Search .............................. 222/325–327, 222/391; 606/92–94; 604/61

(56) References Cited

U.S. PATENT DOCUMENTS

| 4,840,294 | A | * | 6/1989 | Ernst ........................... 222/391 |
| 5,058,770 | A | * | 10/1991 | Herold et al. ................ 222/327 |
| 5,137,181 | A | * | 8/1992 | Keller .......................... 222/327 |
| 5,431,654 | A |   | 7/1995 | Nic .............................. 606/92 |
| 5,529,225 | A |   | 6/1996 | Chang ......................... 222/391 |
| 5,553,754 | A |   | 9/1996 | Dentler ........................ 222/391 |
| 5,595,327 | A |   | 1/1997 | Dentler et al. ............... 222/327 |
| 5,720,418 | A | * | 2/1998 | Timmerman et al. ........ 222/391 |
| 5,755,362 | A | * | 5/1998 | Rodriguez, Jr. et al. ..... 222/391 |
| 6,050,453 | A | * | 4/2000 | Kelders et al. .............. 222/391 |

OTHER PUBLICATIONS

U.S. application Ser. No. 09/503,877, Filed Feb. 14, 2000.
U.S. application Ser. No. 09/503,947, Filed Feb. 14, 2000.

* cited by examiner

Primary Examiner—J. Casimer Jacyna
(74) Attorney, Agent, or Firm—Dorsey &Whitney LLP

(57) ABSTRACT

A bone cement delivery apparatus is provided which includes a body, a ram, a trigger mechanism, and a pawl assembly. The body is configured to support a bone cement dispensing container. The ram is carried by the body and is configured to advance relative to the body to urge bone cement from the dispensing container. The trigger mechanism is located on the body and is configured for actuation to advance the ram. The pawl assembly is carried by the trigger mechanism to engage the ram, the pawl assembly comprising a pawl is carried by the trigger mechanism infinitely adjustable in relation with the trigger mechanism between a relatively low force position and a relatively high force position.

34 Claims, 8 Drawing Sheets

BONE CEMENT DELIVERY APPARATUS AND HAND-HELD FLUENT MATERIAL DISPENSING APPARATUS

TECHNICAL FIELD

The invention pertains to handheld dispensing and delivery apparatus for fluent materials. More particularly, this invention relates to material injectors and guns, such as bone cement injectors and caulk guns.

BACKGROUND OF THE INVENTION

Reconstructive bone surgery is a common procedure to replace bone structures. For example, replacement hip surgery uses a prosthetic hip joint to replace a patient's hip joint. Such surgical procedures include removing the hip joint from a femur, packing bone cement within an inner canal of the femur, and positioning the prosthetic hip joint into the bone cement inside the femur. Subsequently, the cement is allowed to harden, thereby securing the hip joint in place.

Bone cement is typically pre-mixed, then delivered to a surgical site while in a fluent state. Accordingly, such bone cement comprises a fluent material. Such fluent material can vary in viscosity. Furthermore, the viscosity of such fluent material can vary over time in the case of bone cement, as the bone cement begins to set or harden during delivery. Accordingly, it is desirable to adjust delivery force or pressure with which a fluent material can be delivered from a hand-held dispensing and delivery apparatus, such as a bone cement injector.

U.S. Patent No. 5,431,654 discloses a bone cement injector having a trigger structure that cooperates with a low force pawl and a high force pawl in order to change actuation force from a discrete, relatively low force to a discrete, relatively high force. Such force change is carried out by changing (or switching) the pawl that is engaged by the trigger structure. However, no provision is made for infinitely adjusting the fulcrum force of a pawl, nor for variably adjusting the fulcrum distance for a single driving pawl. Hence, improvements are needed over the prior art.

BRIEF DESCRIPTION OF THE DRAWINGS

Preferred embodiments of the invention are described below with reference to the following accompanying drawings.

FIG. 3 is a partial breakaway side elevational view of the bone cement delivery apparatus of FIGS. 1 and 2 illustrating the trigger mechanism in a closed position and the pawl assembly with the pawl adjustably set at an intermediate force position.

SUMMARY OF THE INVENTION

An apparatus is provided for varying the delivery force and/or delivery rate for fluent materials utilizing a single, adjustable force pawl assembly and trigger mechanism. One suitable apparatus comprises a bone cement delivery apparatus. Another suitable apparatus comprises a caulk gun suitable for delivering fluent adhesives and sealant materials.

According to one aspect, a bone cement delivery apparatus is provided which includes a body, a ram, a trigger mechanism, and a pawl assembly. The body is configured to support a bone cement dispensing container. The ram is carried by the body and is configured to advance relative to the body to urge bone cement from the dispensing container. The trigger mechanism is located on the body and is configured for actuation to advance the ram. The pawl assembly is carried by the trigger mechanism to engage the ram, the pawl assembly comprising a pawl is carried by the trigger mechanism infinitely adjustable in relation with the trigger mechanism between a relatively low force position and a relatively high force position.

According to another aspect, a hand-held fluent material dispensing apparatus includes a body, a handle, a trigger, a plunger and a driving pawl. The body supports a fluent dispensing container. The handle depends from the body. The trigger is carried by the body for pivotal movement relative to the handle. The plunger is slidably carried by the body. The driving pawl is pivotally carried by the trigger at positionally adjustable locations along the trigger to vary a fulcrum distance of the trigger between a pivot point of the trigger and a pivot point of the pawl, the pawl configured to engage with the plunger, wherein movement of the trigger imparts coaction between the pawl and the plunger to move the plunger relative to the body and cause dispensing of fluent material from the container.

According to yet another aspect, a surgical cement extrusion gun is provided which includes a frame, a piston, a trigger, and a driving pawl. The frame carries a container having surgical bone cement. The piston communicates with the container and is carried for axial translation by the frame to urge bone cement from the container. The trigger advances the piston to dispense bone cement from the container, and the positionally adjustable driving pawl is interposed between the piston and the trigger and is configured to adjust mechanical advantage between the piston and the trigger so as to vary delivery force imparted to the surgical bone cement within the dispensing container.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Reference will now be made to a preferred embodiment of Applicant's invention. An exemplary implementation is described below and depicted with reference to the drawings comprising a surgical bone cement delivery apparatus. While the invention is described by way of a preferred embodiment, it is understood that the description is not intended to limit the invention to such embodiment, but is intended to cover alternatives, equivalents, and modifications which may be broader than the embodiments, but which are included within the scope of the appended claims.

In an effort to prevent obscuring the invention at hand, only details germane to implementing the invention will be described in great detail, with presently understood peripheral details being incorporated by reference, as needed, as being presently understood in the art.

Figure 1:
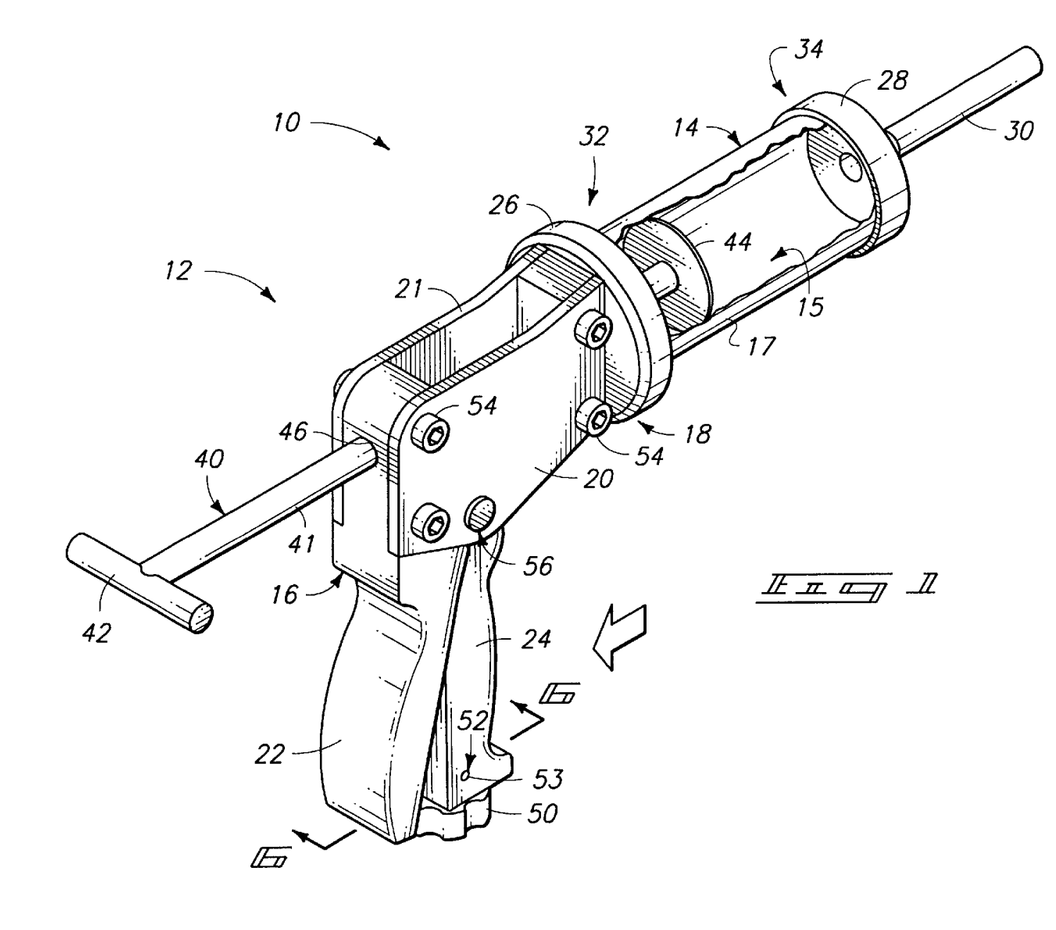
FIG. 1 is a perspective view of a dispensing apparatus embodying the present invention shown in one example in the form of a bone cement delivery apparatus having a pawl assembly including a single, adjustable driving pawl for varying delivery pressure and rate of delivery for fluent bone cement.
Figure 2:
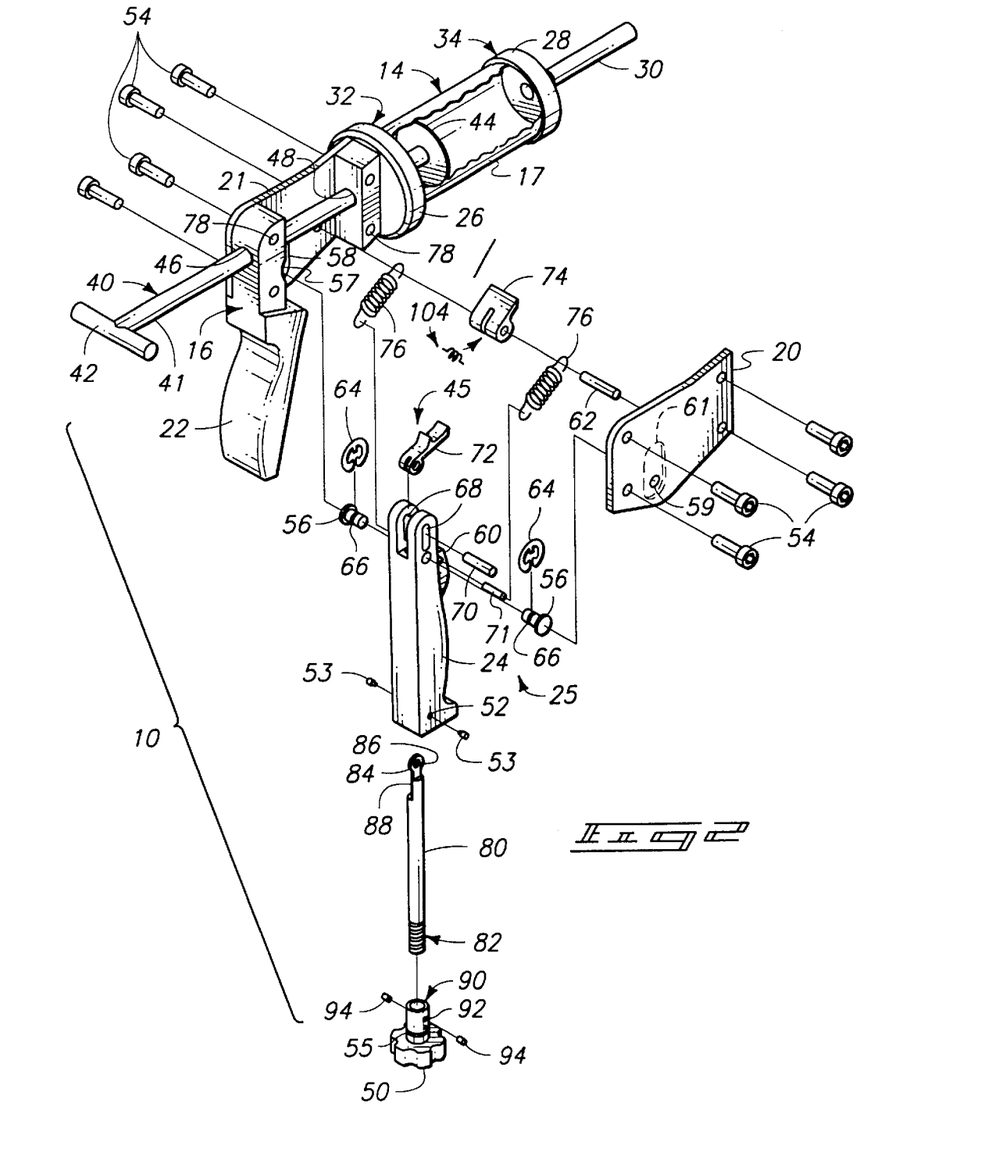
FIG. 2 is an exploded, perspective view of the bone cement delivery apparatus of FIG. 1 illustrating the arrangement of individual components making up the delivery apparatus.

A dispensing apparatus, or injector, for fluent material is illustrated below with reference to FIGS. 1–10 and identified by reference numeral 10. As shown in FIGS. 1 and 2, dispensing apparatus 10 in one embodiment comprises a surgical bone cement delivery apparatus 12, such as a cement gun. However, it is understood that any fluent material can be delivered via dispensing apparatus 10. For example, dispensing apparatus 10 in an alternative embodiment comprises a caulk gun for delivering fluent adhesive or sealant material.

Delivery apparatus 12 comprises a dispensing container, or cartridge, 14 for containing fluent material such as previously mixed surgical bone cement. Dispensing container 14 is removably mated and demated from a cartridge support 26 of a gun body, or frame, 16 using a connector assembly 32. Body 16 is configured to removably support dispensing container 14 via connector assembly 32. A similar connector assembly 34 enables mating and demating of a nozzle 28 and tubular dispensing tip 30 from a cartridge tube 17 of dispensing container 14. Tube 17 cooperates with cartridge support 26 and nozzle 28 so as to define a cartridge cavity 15 in which fluent materials such as bone cement are contained. Each of connector assemblies 32 and 34 comprises a quick-release set of connectors comprising a male portion and a female portion (not numbered).

Further details of dispensing container 14, including connector assemblies 32 and 34, and cartridge tube 17 are described in U.S. patent application Ser. No. 09/503,877, entitled "Connector Assembly for Mating Components, Connector Assembly for a Bone Cement Mixing and Delivery System, and Bone Cement Container Having a Connector Assembly", herein incorporated by reference. Such details are omitted herein as they are not relevant to the invention at hand so as to prevent obscuring an understanding of such invention.

Additionally, further details of nozzle 28, tip 30, and tube 17 are described in U.S. patent application Ser. No. 09/503, 947, entitled "Delivery Apparatus, Nozzle, and Removable Tip Assembly", herein incorporated by reference. Such details are omitted herein as they are not relevant to the invention at hand so as to prevent obscuring an understanding of such invention.

Body 16 of gun 12 comprises a rear receiving member 18 provided by cartridge support 26 and onto which dispensing container 14 is removably mated via connector assembly 32. A female portion of connector assembly 32 comprises cartridge support, or end cap, 26. A pair of spaced-apart side plates 20 and 21 are removably mated onto body 16 using a plurality of threaded fasteners 54 which extend through each of side plates 20 and 21 to mate in engagement with threaded apertures 78 of body 16. Side plates 20 and 21 facilitate assembly of apparatus 10. A handle 22 depends from body 16 from which handle 22 is integrally formed. Side plates 20 and 21 join together handle 22 and cartridge support 26 so as to form body 16. A trigger 24 is pivotally carried by body 16 about a pivot access defined by a pair of lever pins 56. Lever pins 56 support trigger 24 for pivotal movement relative to body 16 and handle 22.

According to one construction, handle 22 and cartridge support 26 are formed from an anodized alloy material, such as anodized aluminum. Side plates 20 and 21 are formed from a stainless steel material. Additionally, trigger 24 is formed from a stainless steel material. Remaining components, such as those that co-act with adjacent components, can be formed from hardened stainless steel material. For example, pawls 72 and 74 can be formed from a hardened stainless steel material. Optionally, or additionally, components can be constructed from composite materials, metals, or other suitable alloys, as understood in the art.

A trigger mechanism 25 comprises handle 22 and trigger 24. Accordingly, trigger mechanism 25 is provided on body 16, and is configured for actuation by a user to dispense bone cement from cartridge 14, as described below in greater detail.

More particularly, a ram, or plunger, 40 is carried by body 16 for slidable and axial reciprocation relative thereto. More particularly, rod 41 is received within respective slidable bores, or bushings, 46 (see FIG. 1) and 48 (see FIG. 2) of body 16. Ram 40 is configured to advance relative to body 16 in order to urge bone cement from dispensing container 14. In operation, trigger mechanism 25 of body 16 is configured for tactile actuation by a user in order to advance ram 40 forward into dispensing container 14. Ram 40 comprises a cylindrical piston rod 41, a T-handle 42, and a piston head 44. Piston head 44 is formed at a forward end of rod 41, whereas T-handle 42 is formed at a trailing end of rod 41.

Figure 4:
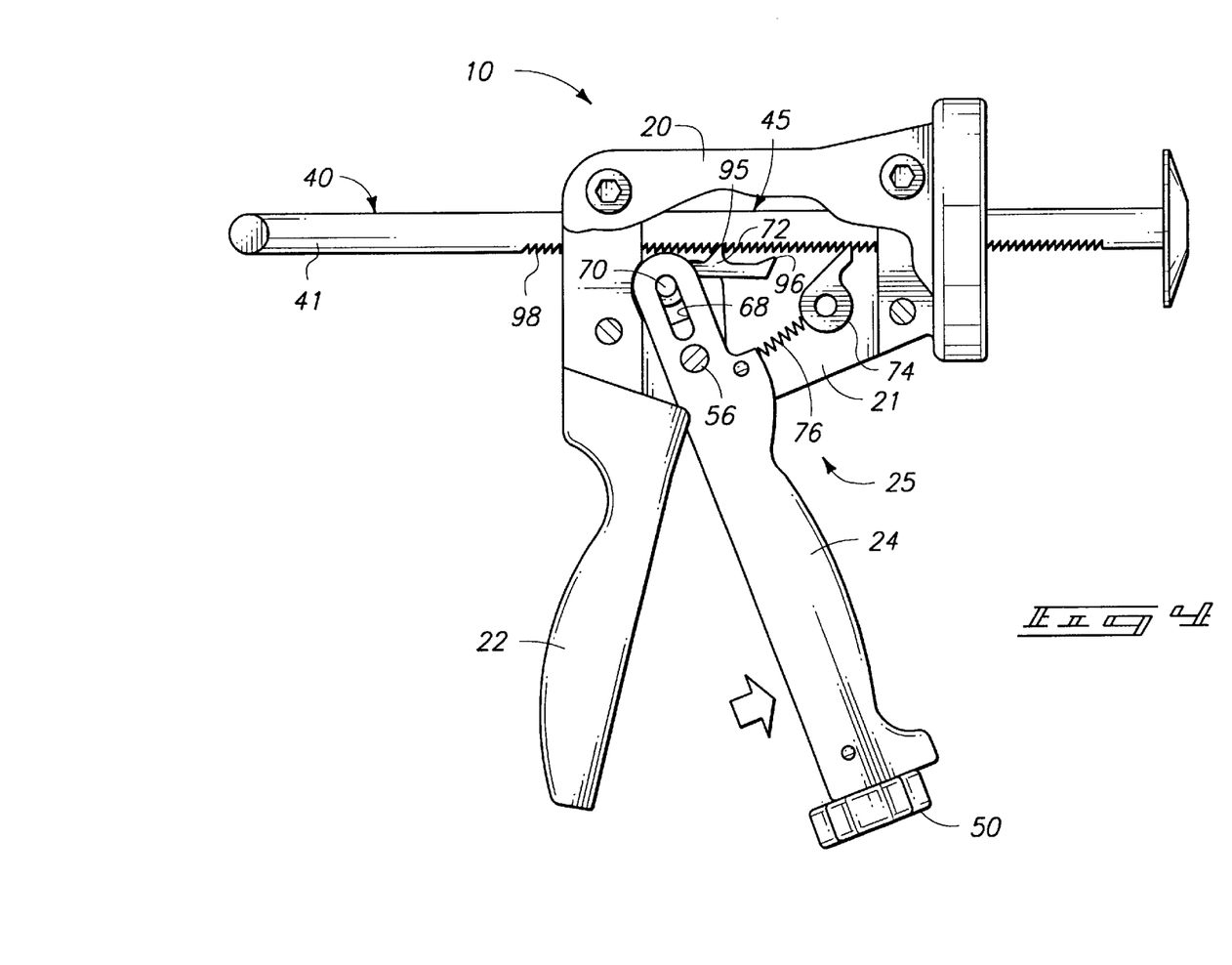
FIG. 4 is a partial breakaway side elevational view corresponding with FIG. 3 and illustrating the trigger mechanism in an open position and the pawl assembly with the pawl adjustably set at an extreme low force position.
Figure 5:
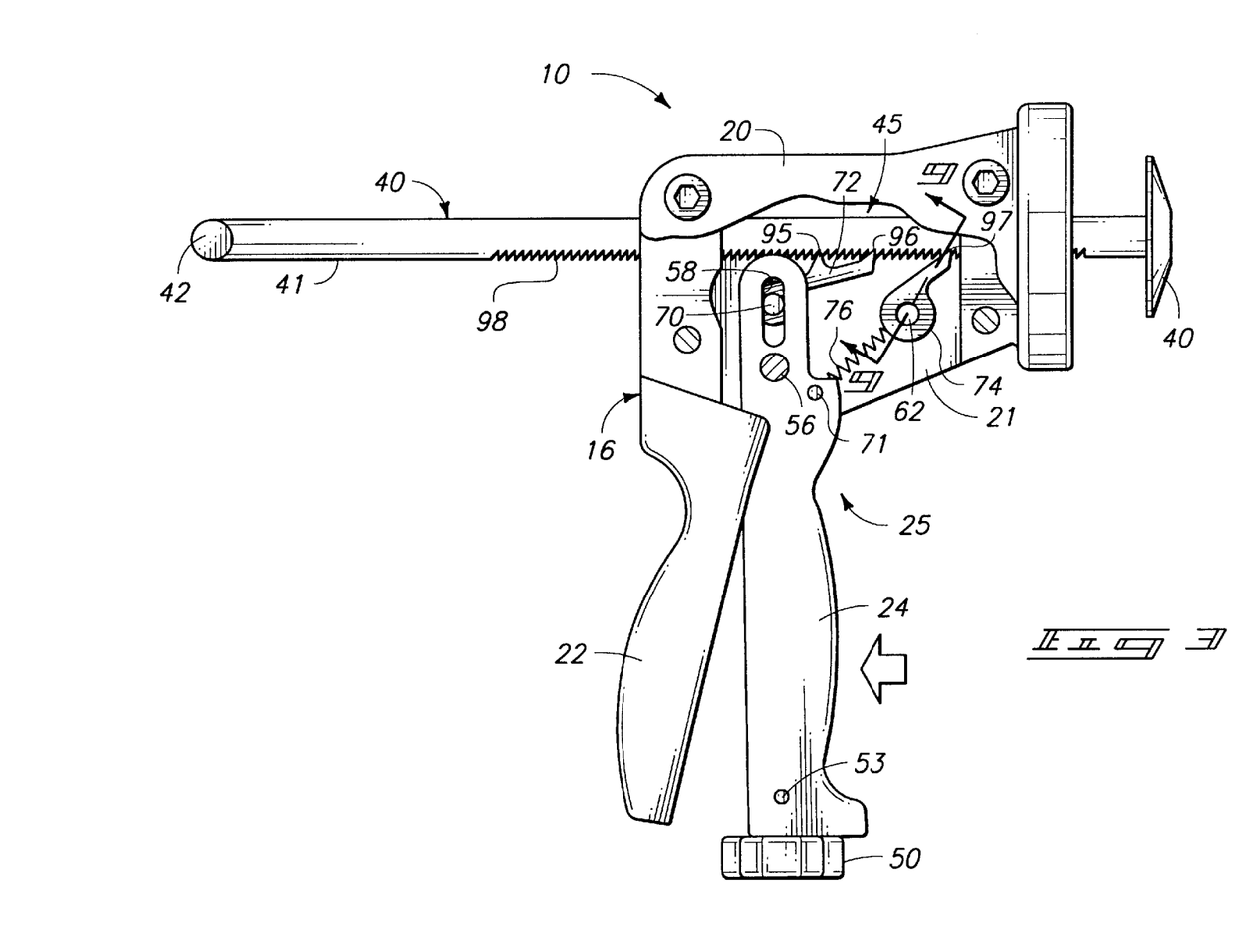
FIG. 5 is a partial breakaway side elevational view corresponding with FIGS. 3 and 4 and illustrating the trigger mechanism in an open position and the pawl assembly with the pawl adjustably set at an extreme high force position.
Figure 6:
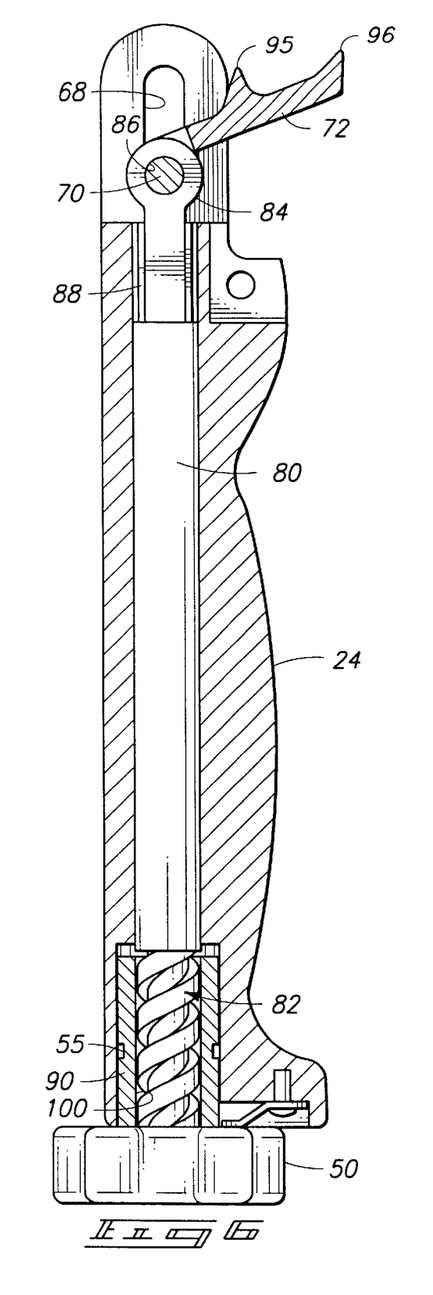
FIG. 6 is a vertical, centerline sectional view of the trigger taken along line 6—6 of FIG. 1 and showing the central pawl pivot adjustment shaft in full side view corresponding with the high force position of FIG. 5.
Figure 7:
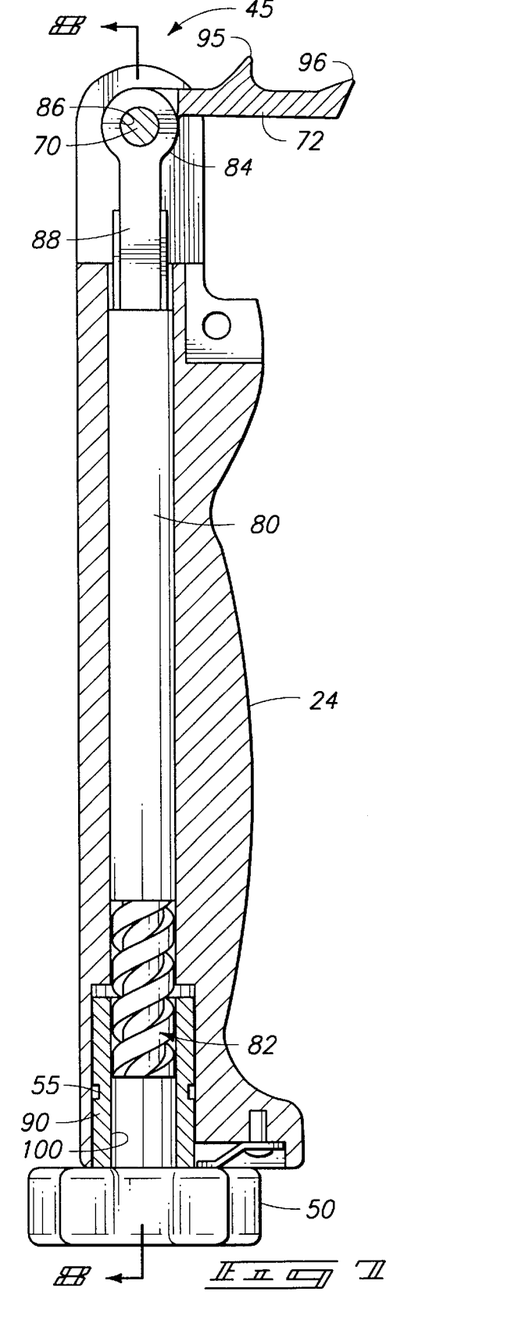
FIG. 7 is a vertical, centerline sectional view corresponding with FIG. 6 and showing the low force position of FIG. 4.

A pawl assembly 45, as shown in FIG. 2, is carried by trigger mechanism 25 to engage ram-40. More particularly, pawl assembly 45 comprises a pawl 72. Pawl 72 is carried by trigger mechanism 25 in infinitely adjustable relation with trigger mechanism 25, between a relatively low force position (as shown in FIGS. 4 and 7) and a relatively high force position (as shown in FIGS. 5 and 6).

Accordingly, pawl assembly 45 comprises a slidably adjustable pivot point for pawl 72, as described below with reference to FIGS. 3–8. A slidably adjustable pivot point comprises a pair of elongate slots 68 provided within trigger 24. Slots 68 each extend generally radially from a pivot point that is defined by lever pins 56. Pawl 72 comprises a traveling eyelet pin 70 that is carried by pawl 72. Preferably, pin 70 is forcibly urged into a bore within pawl 72 to form a pivot pin where pin 70 is forcibly and frictionably received. More particularly, pawl 72 is assembled between slot 68, after which pin 70 is inserted through slot 68 as pin 70 is forcibly and frictionably press fit into pawl 72 so as to be frictionably retained therein. Slots 68 are sized so as to retain pin 70 for slidable and infinitely adjustable positioning along slot 68.

As shown in FIG. 2, pawl assembly 45 is formed between pawl 72 and trigger 24. More particularly, a pivot adjuster shaft 80 is carried internally of trigger 24 for extension and retraction in coaxial relation therein. An eyelet 84 formed in a top end of shaft 80 receives pin 70, wherein pawl 72 is supported by pin 70 for rotation about eyelet 84. Furthermore, pin 70 is sized to be slidably positioned along slots 68.

An adjuster knob 50 is carried for rotation by trigger 24 so as to interact with shaft 80 to impart upward and downward motion of shaft 80 relative to trigger 24 in a manner that adjusts the pivot point for pawl 72. Accordingly, adjuster knob 50, as shown in FIGS. 1 and 2, is also retained to prevent axial movement of knob 50 relative to trigger 24. Such retention is implemented using a pair of threaded pins 53 which are received within complementary, threaded pin bores 52 of trigger 24.

More particularly, a circumferential groove 55 is provided in a tubular shank 90 (see FIG. 2) of knob 50 into which pins 53 are received. Pins 53 are threaded into a body of trigger 24, with a dimple portion of pins 53 (see FIG. 8) being relatively loosely received within groove 55 such that knob 50 is rotatably supported by trigger 24. Hence, adjuster knob 50 is retained against axial movement along a bottom portion of trigger 24. Furthermore, a pair of thread pins 94 each provide a threaded member that interdigitates with a respective threaded portion 82 of shaft 80, as described below with reference to FIG. 8.

In operation, rotation of knob 50 via tactile manipulation by a user imparts axial translation to shaft 80 which moves traveling eyelet pin 70 within slots 68 so as to adjust a fulcrum distance between pawl 72 and lever pins 56. Accordingly, mechanical advantage between ram 40 and trigger 24 is varied by adjusting the positioning of pin 70 within slots 68. Further details of pins 53 and slots 68 are described below with reference to FIG. 8. Accordingly, the need for multiple drive pawls is eliminated. Furthermore, the need for a switching mechanism between pawls is eliminated.

Accordingly, movement of traveling eyelet pin 70. within slots 68 changes a fulcrum length of pawl 72 relative to a pivot axis defined by lever pins 56. Such change in fulcrum length imparts a respective change in mechanical advantage between trigger 24, pawl 72 and ram 40.

A bore 60 within trigger 24 is sized to frictionally receive a spring retention pin 71. Bore 60 extends through a rib of trigger 24 such that pin 71 projects outwardly from either side of bore 60. Pin 71 extends sufficiently out of either side of bore 60 to receive an end loop at one end of a respective tension spring 76. Tension springs 76 are affixed at opposite ends with pins 62 via end loops such that trigger 24 is urged under spring tension to a forward position disposed away from handle 22. Trigger 24 pivots about lever pins 56, with springs 76 retaining trigger 24 in a resting position spaced apart from handle 22.

A bore 57 is provided within side plate 21 of body 16. A slot 58 is milled into an inner surface of such body 16, about bore 57. A similar bore 59 extends through side plate 20, with a similar slot 61 formed in an inner surface of side plate 20, about bore 59. Pins 56 are each supported in body 16 and side plate 20, respectively, utilizing circumferential groove 66 in each pin 56 in cooperation with respective C-clips 64 which trap pins 56 within bores 57 and 59, respectively. Slots 58 and 61 are milled into the inner surfaces of side plates 20 and 21, respectively, to facilitate insertion of clips 64 onto pins 56 during assembly. Bores 57 and 59 each receive a lever pin 56 so as to provide a pivot point for trigger 24 relative to body 16. A non-return pawl 74 is rotatably carried by pin 62, between side plates 20 and 21. As is described below in greater detail, non-return pawl 74 is rotatably urged upwardly against piston rod 41 to prevent rearward retraction of ram 40 due to pressurization of fluent material within dispensing container 14, after actuation of trigger 24 has been completed.

As further shown in FIG. 2, threaded segment 82 comprises a pair of helical Acme threads, or a twin helix Acme thread construction. Eyelet 84 includes a bore 86 into which traveling eyelet pin 70 is received for rotation therein. As will be described below in greater detail, eyelet 84 is constructed as a separate piece, then laser welded onto shaft 80 in abutment with an integrally formed finger 88 of shaft 80. Alternatively, eyelet 84 can be machined directly from a common piece of stock cylindrical material so as to be integrally formed from shaft 80.

Adjuster knob 50 includes thread segments which are provided in the form of threaded pins 94 that are received in respective threaded bores 92 on opposite sides of a tubular shank 90 of knob 50. An inward end of threaded pins 94 is received within a respective thread raceway of threaded segments 82 so as to provide threaded inter-engagement between knob 50 and shaft 80. Rotation of knob 50 imparts upward and downward translation to shaft 80 and pin 70 so as to change a fulcrum length for pawl 72 about pins 56.

Accordingly, threaded segment 82 comprises a pair of inter-nested Acme threads provided along a distal end of shaft 80. Adjuster knob 50 includes thread members, each comprising a respective thread pin 94 configured to ride within a respective one of the threads of threaded segment 82. In response to rotation of knob 50, shaft 80 is carried for axial translation coaxially within trigger 24.

FIG. 2 illustrates in breakaway view details of trigger mechanism 25 and pawl assembly 45 wherein driving pawl 72 is adjustably set at an intermediate force position. More particularly, traveling eyelet pin 70 is shown in an intermediate location within slots 68. Trigger 24 is shown in a depressed, or closed, position, with pawl 72 co-acting with ram 40 to drive piston head 44 forward into dispensing container 14.

As shown in FIG. 3, adjustable pawl 72 includes individual fingers 95 and 96 which engage individual serrated teeth 98 within rod 41 of ram 40. Teeth 98 are biased such that fingers 95 and/or 96 forwardly bias and engage rod 40, but fingers 95 and 96 slide over teeth 98 as trigger 24 is released so as to move into an open position, as depicted in FIG. 4. In such a case, fingers 95 and 96 pass over the sloped rearward faces of teeth 98 to a new location, prior to squeezing trigger 24 toward handle 22 in a subsequent ram advancement operation. Upon release of trigger 24, tension springs 76 pull trigger 24 to the open position depicted in FIG. 4.

Figure 9:
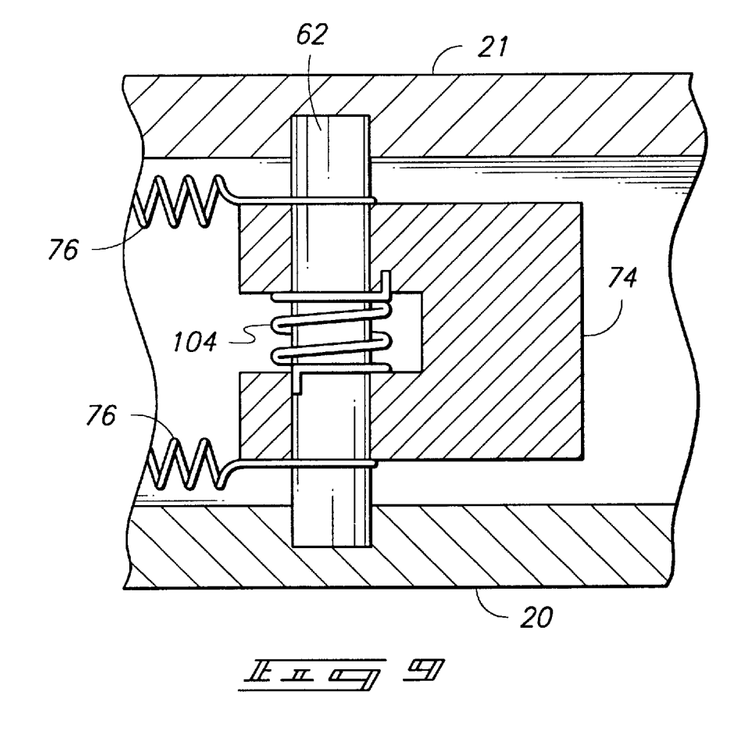
FIG. 9 is a partial breakaway sectional view taken along line 9—9 of FIG. 3 illustrating the arrangement of biasing springs associated with the non-return pawl.

Non-return pawl 74 is biased using a coil spring as depicted in FIG. 9. Non-return pawl 74 further engages via a finger 97 with teeth 98 so as to prevent rearward displacement of ram 40 due to pressurization of fluent material within dispensing container 14. Such pressurization results following advancement of ram 40 due to rearward deployment of trigger 24 during a ram advancement operation. The helical spring on pawl 74 enables pawl 74 to be rotatably biased away from teeth 98 as rod 41 is forwardly advanced via such advancement operation during rearward manipulation of trigger 24. However, rotational engagement of pawl 74 via such spring prevents inadvertent rearward slippage of ram 40 as trigger 24 is released toward an open position.

As shown in FIG. 3, adjustable driving pawl 72 comprises a pair of finger projections 95 and 96 and a pivot pin provided by traveling eyelet pin 70. Finger projections 95 and 96 are spaced apart from one another radially relative to pivot pin 70. Trigger mechanism 25 comprises handle 22 which depends from body 16. Trigger 24 is pivotally carried by body 16, wherein ram 40 is advanced with pawl assembly 45 by urging together handle 22 and trigger 24.

FIG. 4 illustrates the positioning of trigger assembly 25 and pawl assembly 45 wherein trigger 24 is released and pawl assembly 45 is set in an extreme low force position. More particularly, tension springs 76 pull trigger 24 away from handle 22 which moves pawl 72 rearwardly along ram 40 so as to engage additional teeth 98 in rod 41.

According to FIG. 4, traveling eyelet pin 70 has been moved to a highest-most position within slots 68 which corresponds with an extremely low force position for driving ram 40. In such position, pawl 72 engages teeth 98 with only finger 95. However, articulation of trigger 24 as trigger 24 is closed toward handle 22 will change the orientation and mating of finger 96 with teeth 98, particularly when pin 70 is lowered within slots 68. It is understood that rotation of knob 50 adjustably positions pin 70 within slots 68, as described below in greater detail with reference to FIGS. 6–8.

By turning knob 50 clockwise or counterclockwise, axial translation of the shaft within trigger 24 imparts infinitely adjustable positioning of traveling eyelet pin 70 within slots 68. Accordingly, the mechanical advantage between pawl 72 and handle 22 can be adjusted.

More particularly, the distance between pin 70 and lever pins 56 defines a first fulcrum distance. The distance between lever pins 56 and the center of effort exerted on trigger 24 by a user's hand defines a second fulcrum distance. The ratio of the second fulcrum distance over the first fulcrum distance relates to the mechanical advantage imparted to fingers 95 and/or 96 as such fingers interdigitate with teeth 98 so as to forwardly advance ram 40 during delivery of fluent materials from a dispensing container. The provision of knob 50 enables a user to select any of a number of positions defined within the range provided by slots 68 by merely rotating knob 50 to a desired position. Such rotation generates a desirable mechanical advantage and pressurization of fluent material. Accordingly, an operator can more carefully tailor the desired pressure with which fluent material is ejected from a dispensing container via co-action of trigger 24 with handle 22.

Although it is understood that a pair of elongate slots 68 are provided within trigger 24, a single slot could be configured to receive pin 70 so as to achieve a similar result, according to an alternative embodiment. Hence, pawl assembly 45 comprises a single pawl 72 that is pivotally carried by trigger mechanism 25 at continuously adjustable locations along trigger mechanism 25. Such construction allows a user to vary mechanical advantage between trigger mechanism 25 and pawl assembly 45 in order to vary the force that is applied to ram 40 by pawl 72 for a given trigger action force. In some cases, varied delivery force will vary the delivery rate of fluent material.

FIG. 5 illustrates trigger mechanism 25 in an open position and with pawl assembly 45 adjustably set at an extreme high force position. More particularly, traveling eyelet pin 70 is retracted to a lower-most position within slots 68 via rotation of knob 50 in a corresponding clockwise direction. Such position of pin 70 within slots 68 increases the mechanical advantage between trigger 24 and pawl 72, about lever pins 56. In such position, only finger 96 is seen to engage with teeth 98 of rod 41.

As is understood in the art, teeth 98 form a serrated surface along rod 41. In order to retract ram 40 relative to body 16, a user merely rotates rod 41 by grasping and rotating T-handle 42 such that teeth 98 are provided along a topmost surface of rod 41. In such position, pawls 72 and 74 can be readily slid along a corresponding smooth surface of rod 41 during retraction of ram 40 via a user pulling rearwardly along T-handle 42. Once retracted, a user merely needs to rotate T-handle 42 so as to bring teeth 98 into engagement with pawls 72 and 74. Such construction is readily understood within the art and further details are not described herein.

FIG. 6 illustrates in partial vertical centerline sectional view details of trigger 24, with pawl assembly 45 adjustably set at a high force position corresponding with that shown in FIG. 5. More particularly, FIG. 6 illustrates the retraction of shaft 80 to a downward position caused by rotating knob 50 in a clockwise orientation wherein pins 53 co-act with a pair of thread raceways of threaded segment 82 of shaft 80 (see FIG. 8). As shown in FIG. 6, a tubular shank 90 of knob 50 extends within a recess of trigger 24. Threaded portion 82 of shaft 80 extends and retracts within a hollow portion 100 of shank 90. As shown in FIG. 6, threaded portion 82 is retracted all the way down within hollow portion 100, whereas threaded portion 82 is extended upwardly within hollow portion 100 (see FIG. 7).

Figure 8:
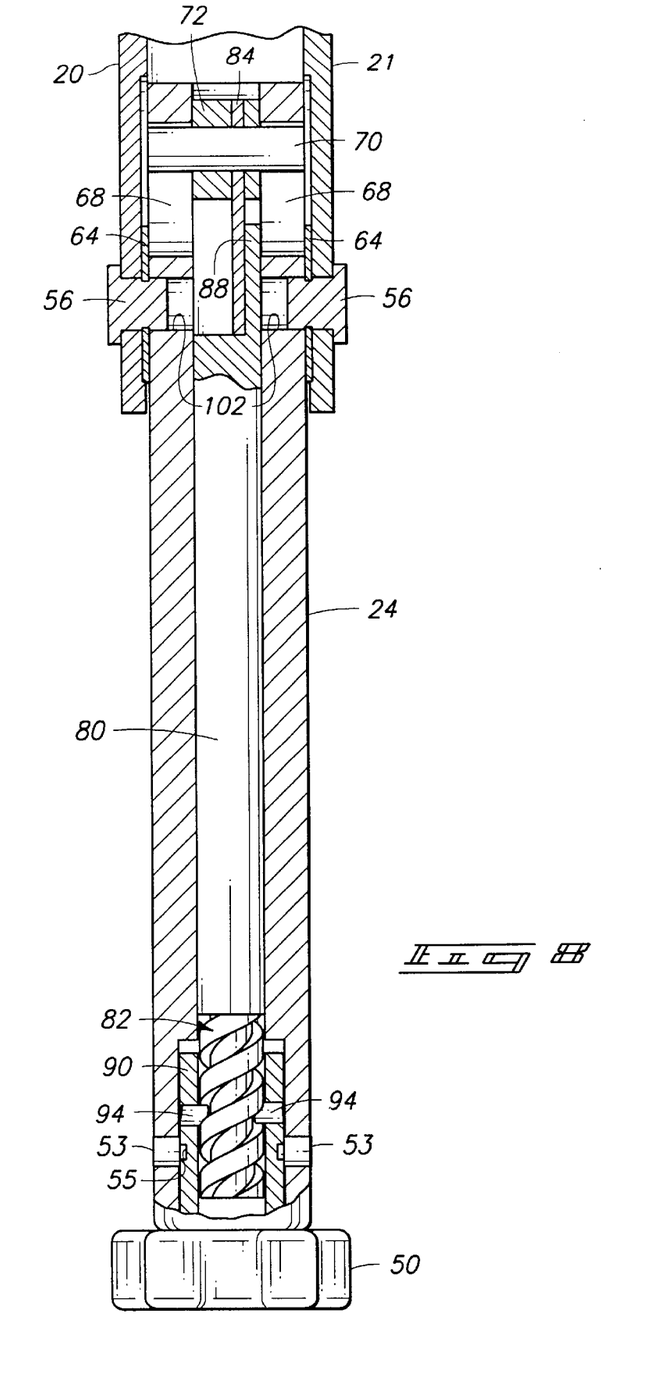
FIG. 8 is a vertical, centerline sectional view of the trigger taken along line 8—8 of FIG. 7 and showing the central pawl pivot adjustment shaft in full side view corresponding with the low force position of FIG. 4.

As shown in FIG. 7, knob 50 has been rotated in a counterclockwise direction, as viewed from the bottom, so as to drive shaft 80 upwardly via coaction of pins 94 of knob 50 with the pair of Acme threads of threaded portion 82 of shaft 80 (see FIG. 8). Accordingly, upward displacement of shaft 80 causes upward displacement of eyelet 84, traveling eyelet pin 70, and pawl 72. As eyelet 84 is extended and retracted, traveling eyelet pin 70 rotates along with pawl 72, within bore 86 of eyelet 84. Furthermore, pin 70 slides within elongate slots 58 (see FIG. 6). Furthermore, the attitude of pawl 72 is seen to change between the positions depicted in FIGS. 6 and 7, as the position of pin 70 is lowered and raised therebetween.

FIG. 8 illustrates the adjustable pawl pivot adjustment features associated with axial displacement of shaft 80 via co-action with rotatable positioning of adjuster knob 50. More particularly, tubular shank 90 of knob 50 includes a circumferential groove 55 provided in an outer face of shank 90. Threaded pins 53 contain an end-nipple that extends within groove 55 in a somewhat loose configuration such that shank 90 (and knob 50) freely rotates within trigger 24. However, knob 50 is prevented from moving axially of trigger 24 via co-acting of pins 53 with groove 55. Rotation of knob 50 further advances and retracts shaft 80 depending on whether knob 50 is rotated clockwise or counterclockwise, as thread segments provided by thread pins 94 engage with respective Acme threads in threaded segment 82.

When viewed from below, clockwise rotation of knob 50 imparts extension of shaft 80 as pins 94 co-act with respective thread raceways within threaded segment 82. Counterclockwise rotation of knob 50 causes downward displacement of shaft 80 as thread pins 94 co-act with respective threads of threaded segment 82. Alternatively, any of a number of different types of threads can be provided along shaft 80 at any of a number of locations.

As shaft 80 is extended and retracted relative to trigger 24, eyelet pin 70 travels within slots 68 between elevated and lowered positions. An elevated position of pin 70 within slot 68 corresponds with a relatively low force position for pawl 72. Lowering of pin 70 to a bottom-most location in slot 68 corresponds with a relatively high force position for pawl 72. Because there is no limit to the number of rotatable positions that knob 50 can be turned relative to trigger 24, the positioning of pin 70 between a topmost and bottom-most position of slot 68 is infinitely adjustable within an end-limited range. Accordingly, a user is enabled with the ability to adjust delivery force (and delivery rate) to nearly any desired position provided within the extreme limits of slot 68.

As further shown in FIG. 8, pins 56 provide a pivot point for trigger 24. Each pin 56 is entrapped via a C-clip 64 onto side plates 20 and 21, within respective bores 102. An inner surface of each pin 56 extends within a bore 102 on either side of trigger 24. Pins 56 thereby provide a pivot point for trigger 24 without preventing axial extension and retraction of shaft 80 within trigger 24.

FIG. 9 illustrates the relationship of the non-return pawl of FIG. 2 relative to tension springs 76 which serve to extend the trigger to an open position, and a torsion spring 104 which cooperates with non-return pawl 74 and pin 62 to upwardly bias pawl 74 into contact with teeth on the shaft of the ram. Alternatively, any of a number of different spring configurations can be utilized to upwardly bias non-return pawl 74 into engagement with the ram so as to prevent rearward displacement of the ram upon release of the trigger.

Figure 10:
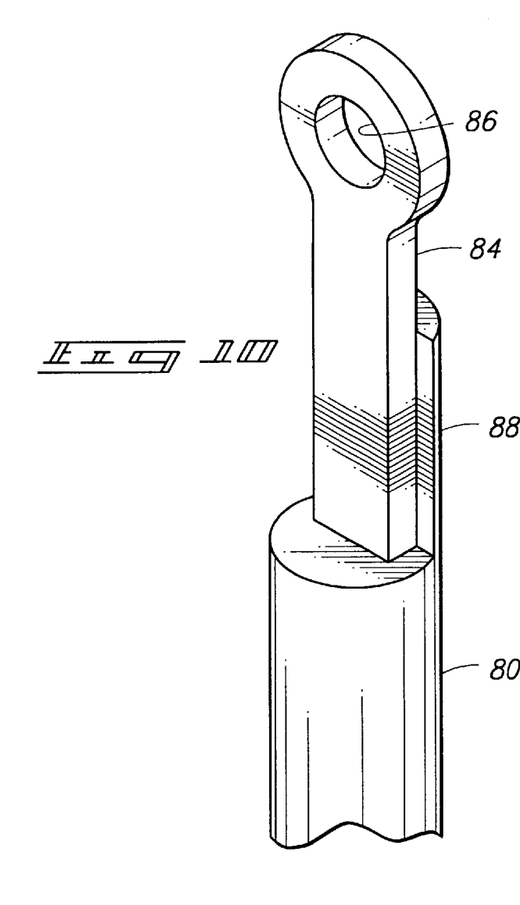
FIG. 10 is a partial perspective view illustrating the construction of an eyelet on an upper end of the central pawl pivot adjustment shaft.

FIG. 10 illustrates one suitable construction for affixing eyelet 84 onto shaft 80. More particularly, shaft 80 is formed from a piece of cylindrical stainless steel material which is machined so as to form a finger 88. Eyelet 84 is machined from a separate piece of similar stainless steel material, after which eyelet 84 is laser welded onto shaft 80 and finger 88. Alternatively, eyelet 84 can be machined directly from shaft 80.

Although the dispensing apparatus of Applicant's invention has been described in FIGS. 1–10 according to one embodiment in the form of a cement gun, it is understood that alternative embodiments can also exist. For example, the dispensing apparatus can comprise a caulk gun. Accordingly, it is understood that, more generically, a hand-held fluent material dispensing apparatus is provided by Applicant's invention. The dispensing apparatus includes a body, a handle, a trigger, a plunger, and a driving pawl. The body supports a fluent material dispensing container. The handle depends pivotally from the body. The trigger is carried by the body for pivotal movement relative to the handle. The plunger is slidably carried by the body. The driving pawl is pivotally carried by the trigger at positionally adjustable locations along the trigger in order to vary a fulcrum distance of the trigger between a pivot point of the trigger and a pivot point of the pawl. The pawl is configured to engage with the plunger. In operation, movement of the trigger imparts co-action between the pawl and the plunger in order to move the plunger relative to the body and to cause dispensing the fluent material from the container.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A bone cement delivery apparatus, comprising:
   a body configured to support a bone cement dispensing container;
   a ram carried by the body and configured to advance relative to the body to urge bone cement from the dispensing container;
   a trigger mechanism on the body and configured for actuation to advance the ram; and
   a pawl assembly carried by the trigger mechanism to engage the ram, the pawl assembly comprising a pawl carried by the trigger mechanism infinitely adjustable in relation with the trigger mechanism between a relatively low force position and a relatively high force position, the trigger mechanism including an elongate pivot slot for pivotally supporting the pawl at infinitely adjustable locations.

2. The bone cement delivery apparatus of claim 1 wherein the trigger mechanism comprises a trigger pivotally carried by the body about a pivot axis, and wherein the pawl assembly comprises a slidably adjustable pivot point for the pawl.

3. The bone cement delivery apparatus of claim 2 wherein the slidably adjustable pivot point comprises an elongate slot within the trigger extending generally radially from the pivot point and the pawl comprises a traveling eyelet pin carried by the pawl, received within the slot, and movable to infinitely adjustable positions along the slot.

4. The bone cement delivery apparatus of claim 3 further comprising a shaft carried for extension and retraction relative to the trigger, wherein the traveling eyelet pin is supported by the shaft for movement therewith.

5. The bone cement delivery apparatus of claim 4 wherein the shaft comprises a threaded portion, and further comprising an adjustor knob carried for rotation relative to the trigger, retained from axial movement, and comprising a thread member interdigitating with the threaded portion of the shaft, wherein tactile rotation of the adjustor knob imparts axial translation of the shaft so as to move the eyelet travel pin within the slot.

6. The bone cement delivery apparatus of claim 5 wherein movement of the eyelet travel pin changes a fulcrum length of the pawl relative to the pivot axis so as to impart a change in mechanical advantage between the trigger, the pawl and the ram.

7. The bone cement delivery apparatus of claim 5 wherein the threaded portion comprises a pair of inter-nested acme threads provided along a distal end of the shaft, and wherein the adjustor knob includes a pair of the thread members each comprising a thread pin configured to ride within a respective one of the threads.

8. The bone cement delivery apparatus of claim 4 wherein the shaft is carried for axial translation coaxially within the trigger.

9. The bone cement delivery apparatus of claim 8 wherein the shaft comprises an eyelet, a threaded portion, and a pivot mechanism coincident with the pivot axis and intermediate the eyelet and the threaded portion.

10. The bone cement delivery apparatus of claim 9 wherein axial translation of the shaft within the trigger imparts infinitely adjustable positioning of the eyelet travel pin within at least one elongate slot of the trigger so as to adjust mechanical advantage between the trigger, the pawl, and the ram.

11. The bone cement delivery apparatus of claim 9 wherein the trigger comprises a pair of elongate slots sized to slidably receive the eyelet travel pin.

12. The bone cement delivery apparatus of claim 9 wherein the pawl comprises a plurality of drive fingers spaced-apart as relates to the traveling eyelet pin and the ram comprises a plurality of axially spaced-apart teeth configured to receive at least one of the drive fingers.

13. The bone cement delivery apparatus of claim 1 wherein the pawl assembly comprises a pawl pivotally carried by the trigger mechanism at continuously adjustable locations along the trigger mechanism so as to vary mechanical advantage between the trigger mechanism and the pawl assembly to vary force applied to the ram by the pawl.

14. The bone cement delivery apparatus of claim 13 wherein the pawl comprises a pair of finger projections and a pivot pin, the finger projections spaced apart from one another radially of the pivot pin.

15. The bone cement delivery apparatus of claim 1 wherein the trigger mechanism comprises a handle depending from the body and a trigger pivotally carried by the body, wherein the ram is advanced with the pawl assembly by urging together the handle and the trigger.

16. A handheld fluent material dispensing apparatus, comprising:
a body for supporting a fluent dispensing container;
a handle depending from the body;
a trigger carried by the body for pivotal movement relative to the handle;
a plunger slidably carried by the body; and
a driving pawl pivotally carried by the trigger at positionally adjustable locations along the trigger to vary a fulcrum distance of the trigger between a pivot point of the trigger and a pivot point of the pawl, the pawl configured to engage with the plunger, the driving pawl being pivotally carried by the trigger at continuously adjustable locations along the trigger so as to vary mechanical advantage between the trigger and the pawl in order to vary force supplied to the plunger by the pawl;
wherein movement of the trigger imparts coaction between the pawl and the plunger to move the plunger relative to the body and cause dispensing of fluent material from the container.

17. The material dispensing apparatus of claim 16 wherein the trigger comprises an adjustment shaft carried for coaxial movement within the trigger, the shaft comprising an eyelet for receiving an eyelet pin, wherein the pawl is carried for rotation by the eyelet pin relative to the eyelet.

18. The material dispensing apparatus of claim 17 wherein the shaft comprises a pair of elongate slots extending axially of the shaft, opposite one another, the slots configured to receive the eyelet pin so as to provide an adjustable position pivot point for the pawl along the trigger.

19. The material dispensing apparatus of claim 18 further comprising an adjustment member axially fixed on the trigger for rotation, wherein the shaft comprises a first thread member and the adjustment member comprises a second, complementary thread member, and wherein rotation of the adjustment member imparts axial displacement of the shaft within the trigger.

20. The material dispensing apparatus of claim 16 wherein the plunger comprises a ram including a piston rod and piston provided on a leading end of the piston rod, and wherein the piston rod further comprises a plurality of teeth extending axially along the piston rod configured to engage with at least one finger of the driving pawl, wherein the driving pawl engages with the piston rod via the teeth to drive the piston forward against a fluent material.

21. The material dispensing apparatus of claim 16 further comprising a pair of opposed lever pins carried in axially coincident relation by the body and cooperating with the trigger to provide a pivot mechanism for rotatably supporting the trigger from the body for movement relative to the handle.

22. The material dispensing apparatus of claim 16 further comprising a shaft coaxially located within the trigger for extension and retraction relative to the trigger and operative to positionally adjust location of the pivot point for the driving pawl.

23. The material dispensing apparatus of claim 22 wherein the driving pawl comprises a traveling eyelet pin, wherein the handle comprises at least one elongate slot configured to receive the traveling eyelet pin slidably therein, and wherein the shaft is coupled in rotatable relation with the traveling eyelet pin to movably position the pivot point for the driving pawl in relation to the handle as the shaft is extended and retracted.

24. The material dispensing apparatus of claim 23 wherein the shaft comprises a threaded portion, and further comprising an adjuster knob rotatably carried by the trigger and retained from axial movement, and further comprising a thread member provided in the adjustor knob and configured for interdigitating communication with the threaded portion of the shaft, wherein rotatable manipulation of the adjustor knot imparts axial translation to the shaft so as to move the pivot point of the driving pawl.

25. A surgical cement extrusion gun, comprising:
a frame for carrying a container having surgical bone cement;
a piston communicating with the container and carried for axial translation by the frame to urge bone cement from the container;
a trigger for advancing the piston to dispense bone cement from the container; and
a positionally adjustable driving pawl interposed between the piston and the trigger and configured to adjust mechanical advantage between the piston and the trigger so as to vary delivery force imparted to the surgical bone cement within the dispensing container, and
the trigger includes a shaft carried for extension and retraction within the trigger, the shaft comprising an eyelet for pivotally receiving the driving pawl, the driving pawl is carried for rotation by the eyelet via an eyelet pin, and axial extension and retraction of the shaft within the trigger positionally adjusts a pivot point-for the driving pawl relative to the trigger.

26. The surgical cement extrusion gun of claim 25 wherein the frame comprises a body including a support and a handle, wherein the support is configured to removably receive a bone cement cartridge.

27. The surgical cement extrusion gun of claim 26 wherein the body comprises at least one side plate removably received between the support and the handle.

28. The surgical cement extrusion gum of claim 27 wherein the body comprises a pair of laterally spaced-apart side plates removably received between the dispensing container support and the handle, and wherein the trigger is supported for pivotal movement between the pair of side plates.

29. A bone cement delivery apparatus, comprising:

a body configured to support a bone cement dispensing container;

a ram carried by the body and configured to advance relative to the body to urge bone cement from the dispensing container;

a trigger mechanism on the body and configured for actuation to advance the ram; and a pawl assembly carried by the trigger mechanism to engage the ram, the pawl assembly comprising a pawl carried by the trigger mechanism infinitely adjustable in relation with the trigger mechanism between a relatively low force position and a relatively high force position;

the trigger mechanism includes a trigger pivotally carried by the body about a pivot axis, the pawl assembly comprising a slidably adjustable pivot point for the pawl; and the slidably adjustable pivot point includes an elongate slot within the trigger extending generally radially from the pivot point and the pawl includes a traveling eyelet pin carried by the pawl, received within the slot, and being movable to infinitely adjustable positions along the slot.

30. The material dispensing apparatus of claim 29 further comprising an adjustment member axially fixed on the trigger for rotation, wherein the shaft comprises a first thread member and the adjustment member comprises a second, complementary thread member, and wherein rotation of the adjustment member imparts axial displacement of the shaft within the trigger.

31. A handheld fluent material dispensing apparatus, comprising:

a body for supporting a fluent dispensing container;

a handle depending from the body;

a trigger carried by the body for pivotal movement relative to the handle;

a plunger slidably carried by the body;

a driving pawl pivotally carried by the trigger at positionally adjustable locations along the trigger to vary a fulcrum distance of the trigger between a pivot point of the trigger and a pivot point of the pawl, the pawl configured to engage with the plunger, and a pair of opposed lever pins carried in axially coincident relation by the body and cooperating with the trigger to provide a pivot mechanism for rotatably supporting the trigger from the body for movement relative to the handle;

the trigger including an adjustment shaft carried for coaxial movement within the trigger, the shaft comprising an eyelet for receiving an eyelet pin, wherein the pawl is carried for rotation by the eyelet pin relative to the eyelet; and the shaft including a pair of elongate slots extending axially of the shaft, opposite one another, the slots being configured to receive the eyelet pin: so as to provide an adjustable position pivot point for the pawl along the trigger, wherein movement of the trigger imparts coaction between the pawl and the plunger to move the plunger relative to the body and cause dispensing of fluent material from the container.

32. A handheld fluent material dispensing apparatus, comprising:

a body for supporting a fluent dispensing container;

a handle depending from the body;

a trigger carried by the body for pivotal movement relative to the handle;

a plunger slidably carried by the body; and a driving pawl pivotally carried by the trigger at positionally adjustable locations along the trigger to vary a fulcrum distance of the trigger between a pivot point of the trigger and a pivot point of the pawl, the pawl configured to engage with the plunger, and a pair of opposed lever pins carried in axially coincident relation by the body and cooperating with the trigger to provide a pivot mechanism for rotatably supporting the trigger from the body for movement relative to the handle, wherein movement of the trigger imparts coaction between the pawl and the plunger to move the plunger relative to the body and cause dispensing of fluent material from the container.

33. A handheld fluent material dispensing apparatus, comprising:

a body for supporting a fluent dispensing container;

a handle depending from the body;

a trigger carried by the body for pivotal movement relative to the handle;

a plunger slidably carried by the body;

a driving pawl pivotally carried by the trigger at positionally adjustable locations along the trigger to vary a fulcrum distance of the trigger between a pivot point of the trigger and a pivot point of the pawl, the pawl configured to engage with the plunger, a shaft coaxially located within the trigger for extension and retraction relative to the trigger and operative to positionally adjust location of the pivot point for the driving pawl; and the driving pawl includes a traveling eyelet pin, the handle includes at least one elongate slot configured to receive the traveling eyelet pin slidably therein, and the shaft is coupled in rotatable relation with the traveling eyelet pin to movably position the pivot point for the driving pawl in relation to the handle as the shaft is extended and retracted, wherein movement of the trigger imparts coaction between the pawl and the plunger to move the plunger relative to the body and cause dispensing of fluent material from the container.

34. The material dispensing apparatus of claim 33 wherein the shaft comprises a threaded portion, and further comprising an adjuster knob rotatably carried by the trigger and retained from axial movement, and further comprising a thread member provided in the adjustor knob and configured for interdigitating communication with the threaded portion of the shaft, wherein rotatable manipulation of the adjustor knot imparts axial translation to the shaft so as to move the pivot point of the driving pawl.

* * * * *